United States Patent
Thys

(10) Patent No.: US 11,116,883 B2
(45) Date of Patent: Sep. 14, 2021

(54) METHOD FOR REMOVING BLOOD FROM AN EXTRACORPOREAL BLOOD CIRCUIT AFTER COMPLETING A BLOOD TREATMENT SESSION, CONTROL AND REGULATING UNIT AND TREATMENT APPARATUS FOR EXECUTING THE METHOD

(71) Applicant: Fresenius Medical Care Deutschland GmbH, Bad Homburg (DE)

(72) Inventor: Martin Thys, Gärtringen (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 0 days.

(21) Appl. No.: 16/334,092

(22) PCT Filed: Sep. 19, 2017

(86) PCT No.: PCT/EP2017/073632
§ 371 (c)(1),
(2) Date: Mar. 18, 2019

(87) PCT Pub. No.: WO2018/054901
PCT Pub. Date: Mar. 29, 2018

(65) Prior Publication Data
US 2019/0358389 A1    Nov. 28, 2019

(30) Foreign Application Priority Data

Sep. 20, 2016  (DE) .................... 10 2016 117 725.3

(51) Int. Cl.
*A61M 1/36*    (2006.01)
(52) U.S. Cl.
CPC .......... *A61M 1/3646* (2014.02); *A61M 1/365* (2014.02); *A61M 1/3609* (2014.02); *A61M 1/3612* (2014.02); *A61M 2230/207* (2013.01)

(58) Field of Classification Search
CPC .............. A61M 1/3646; A61M 1/3609; A61M 1/3612; A61M 1/365; A61M 2230/207
See application file for complete search history.

(56) References Cited

U.S. PATENT DOCUMENTS

| 2003/0100857 A1 | 5/2003 | Pedrazzi et al. |
| 2010/0087772 A1 | 4/2010 | Gronau et al. |
| (Continued) | | |

FOREIGN PATENT DOCUMENTS

| CN | 101511404 A | 8/2009 |
| CN | 203677608 U | 7/2014 |
| (Continued) | | |

OTHER PUBLICATIONS

International Preliminary Report on Patentability in Application No. PCT/EP2017/073632, dated. Mar. 26, 2019, 9 pages (English Translation).

(Continued)

*Primary Examiner* — John Kim
(74) *Attorney, Agent, or Firm* — Fish & Richardson P.C.

(57) ABSTRACT

The present disclosure relates to a method for removing blood and/or blood mixture from an extracorporeal blood circuit with a blood filter used for the blood treatment of a patient, after completing the blood treatment session. The blood filter includes a blood chamber and a spent dialysate chamber, between which a membrane is arranged. The blood chamber is connected to an arterial blood line, a venous blood line, a dialysis inlet line, and a dialysate outlet line. The venous blood line is fluidly connected to the dialysis inlet. The method includes displacing the blood and/or the blood mixture from the blood chamber by introducing substituate into the arterial blood line, and generating a (Continued)

pressure difference in the blood filter with a lower pressure in the spent dialysate chamber and a higher pressure in the blood chamber.

19 Claims, 4 Drawing Sheets

(56) References Cited

U.S. PATENT DOCUMENTS

| | | |
|---|---|---|
| 2010/0274172 A1 | 10/2010 | Guenther et al. |
| 2012/0197174 A1 | 8/2012 | Brotherton et al. |
| 2013/0025697 A1 | 1/2013 | Blasek et al. |
| 2016/0310657 A1 | 10/2016 | Solem et al. |

FOREIGN PATENT DOCUMENTS

| | | |
|---|---|---|
| CN | 104721897 A | 6/2015 |
| DE | 102011108785 | 1/2013 |
| EP | 2583701 | 4/2013 |
| WO | WO 2008/028579 | 3/2008 |
| WO | WO 2010/121750 | 10/2010 |

OTHER PUBLICATIONS

International Search Report and Written Opinion in Application No. PCT/EP2017/073632, dated Dec. 4, 2017, 11 pages (English Translation).

METHOD FOR REMOVING BLOOD FROM AN EXTRACORPOREAL BLOOD CIRCUIT AFTER COMPLETING A BLOOD TREATMENT SESSION, CONTROL AND REGULATING UNIT AND TREATMENT APPARATUS FOR EXECUTING THE METHOD

CROSS-REFERENCE TO RELATED APPLICATIONS

The present application is the national stage entry of International Patent Application No. PCT/EP2017/073632, filed on Sep. 19, 2017, and claims priority to Application No. DE 10 2016 117 725.3, filed in the Federal Republic of Germany on Sep. 20, 2016, the disclosures of which are expressly incorporated herein in entirety.

TECHNICAL FIELD

The present disclosure relates to methods for removing blood and/or a blood mixture from an extracorporeal blood circuit utilized for a blood treatment of a patient after completing a blood treatment session. It further relates to a control and/or regulating unit for executing the methods.

BACKGROUND

After the end of a blood treatment, the blood, which is still present in the extracorporeal circuit, is usually displaced from the extracorporeal blood circuit in direction of the vascular system of the patient by means of a substitute liquid (hereafter also shortly referred to as substituate) and is thus reinfused into the patient. During this, turbulences at the interface between substituate and blood often result in a considerable mixing of these two liquids in tubes and filter fibers. Thus, caused by the process, also a certain amount of substituate is unintentionally infused into the patient until the blood is completely reinfused.

Since removing parts of the liquid fraction from the blood of the patient is usually a therapeutic target, the infusion of substituate is undesired and even counterproductive, as the preceding treatment was expressly intended, amongst others, to remove water from the patients' blood.

SUMMARY

Methods are described herein for removing blood and/or a blood mixture, after completion of a blood treatment session or blood treatment, from an extracorporeal blood circuit with a blood filter, the blood circuit having been used for the blood treatment of a patient. In this, the blood filter comprises a blood chamber and a spent dialysate chamber, between which a membrane is arranged. The blood chamber is connected for the purpose of blood treatment to an arterial blood line leading to the blood chamber and to a venous blood line leading away from the blood chamber. The blood filter is further connected to a fresh dialysis liquid line, which leads to the spent dialysate chamber and to a spent dialysate line, which leads away from the spent dialysate chamber. The method encompasses at least the steps: Displacing the blood and/or the blood mixture from the blood chamber by introducing substituate into the arterial blood line and generating a pressure difference in the blood filter. To this end, a lower pressure is at least temporarily generated or maintained in the spent dialysate chamber than in the blood chamber.

The control unit, which may also be designed as a regulating unit, is suitable and provided and/or programmed and/or arranged and/or configured for executing the method in interaction with a medical blood treatment apparatus. It can optionally comprise further devices such as, for example, storage devices, addition devices, (preferably automated) signal generating devices and so on.

The medical treatment apparatus (hereafter also in short: treatment apparatus) comprises optionally at least one extracorporeal blood circuit having a conduit interior. It is further equipped with at least one blood pump for conveying blood within the conduit interior of the extracorporeal blood circuit, the blood pump being arranged or arrangeable at or in the extracorporeal blood circuit. In addition, it comprises a control or regulating unit.

A storage medium (denoted here also as carrier), in particular a digital one, in particular a non-volatile one, in particular a floppy disk, RAM, ROM, CD, hard disk, USB stick, flash card, SD card, or EPROM, in particular with electronically or optically readable control signals may interact with a programmable computer or computer system such that the machine-induced steps of method described herein are prompted.

In this, all or some of the steps of the method which are executed by the machine may be prompted.

A computer program product comprises a program code or machine control instructions saved on a volatile machine-readable storage medium for prompting the machine-induced steps of the method when the computer program product runs on a computer.

The term machine-readable storage medium, as used herein, denotes in certain embodiments a carrier, which contains data or information which is interpretable by software and/or hardware. The carrier may be a data carrier such as a disk, a CD, DVD, a USB stick, a flashcard, an SD card an EPROM and the like.

A computer program comprises a program code for prompting the machine-induced steps of the method when the computer program runs on a computer.

In this, all, several or some of the steps of the method which are executed by the machine may be prompted.

A computer program product can be understood as, for example, a computer program which is stored on a data carrier, a signal wave, an embedded system as a comprehensive system with a computer program (e.g. an electronic device with a computer program), a network of computer-implemented computer programs (e.g. a client-server system, a cloud computing system, etc.), or a computer on which a computer program product is loaded, executed, saved or developed.

A computer program can be understood as, for example, a physical software product ready for distribution, which contains a computer program.

It also applies to the computer program product and to the computer program that all or some of the steps of the method which are executed by the machine may be prompted.

In all of the following embodiments, the use of the expression "may be" or "may have" and so on, is to be understood synonymously with "preferably is" or "preferably has," and so on respectively, and is intended to illustrate an embodiment.

Whenever numerical words are mentioned herein, the person skilled in the art shall recognize or understand them as indications of numerical lower limits. Unless it leads the person skilled in the art to an evident contradiction, the person skilled in the art shall comprehend the specification for example of "one" encompassing "at least one". This understanding is also equally encompassed by the present invention as the interpretation that a numerical word, for example, "one" may alternatively mean "exactly one", wherever this is evidently technically possible for the person skilled in the art. Both are encompassed by the present invention and apply herein to all used numerical words.

A blood mixture describes a mixture of blood and at least one further fluid, in particular one further liquid. A blood mixture is for example a mixture of blood and substitute, which is e.g. a solution, like e.g. fresh dialysis liquid, physiological saline etc.

A "substitute" may for example be any substitute or fresh dialysis liquid generally known for use in a blood treatment, e.g. for a hemodiafiltration. A substitute is preferably a solution, e.g. isotone saline solution, e.g. a solution containing 0.9% NaCl, which is already used during the blood treatment session and is thus a solution already introduced or introducible through a fluid communication into the extracorporeal blood circuit. The term "substitute" may also mean herein "exchange liquid".

Q describes a flow rate, herein also mentioned in short as flow. $Q_{UF}$ describes the flow rate through an ultrafiltration pump (herein also in short: UF pump), $Q_{BP}$ describes the flow rate through a blood pump, $Q_{substituate\_pump}$ describes the flow rate through a substituate pump, $Q_{conveying\_device}$ describes the flow rate through a conveying device and $Q_{patient}$ describes the flow rate at which the patient is being reinfused with blood or blood mixture.

Embodiments may comprise one or several of the following features in any combination, unless the person skilled in the art recognizes their combination as technically impossible.

In some exemplary embodiments, the medical treatment apparatus comprises a device, e.g. a conveying device like e.g. a substitute pump, blood pump or fresh dialysis liquid pump, which is provided to introduce substitute into the extracorporeal blood circuit, e.g. into the arterial blood line. The conveying device, which is provided for introducing substitute, is referred to hereafter also as conveying device for substitute.

In some exemplary embodiments, one or several of the following actuators or conveying devices are used for the method:
- a conveying device for substitute, in particular a substituate pump and/or a blood pump
- a filter which comprises a semi-permeable membrane and connection on the side of the fresh dialysis liquid or a connection on the side of the device
- A pump, which builds a pressure or negative pressure, which pressure drives a transmembrane flow from the blood side of the filter to the spent dialysate side of the filter. This pump is in some embodiments identical to the pump that conveys substituate. In other embodiments, the two mentioned pumps are not identical to each other, and are embodied separately. In some embodiments the pump, which builds the pressure or negative pressure, is an ultrafiltration pump (short: UF pump). The UF pump generates preferably a negative pressure in the spent dialysate chamber.
- A flow resistance. The flow resistance is preferably situated in the extracorporeal blood circuit on the outflow side of the blood chamber of the blood filter, such that a positive pressure results in the blood chamber due to the flow resistance in connection with the aforementioned pump, which builds up pressure.

In applying the method, the UF pump and the flow resistance, in a suitable embodiment, cause a pressure difference between the blood side of the filter and the spent dialysate side of the filter, whereby a transmembrane flow from the blood side of the filter to the spent dialysate side of the filter results. In this, preferably water and possibly low molecular components are pressed or drawn from the blood side to the spent dialysate side while cellular components remain on the blood side such that the hematocrit on the blood side may increase.

As it is known from the prior art, the blood return begins in some embodiments—preferably immediately—after the completion of the actual therapy. The patient's blood is then, preferably according to a doctor's prescription (which may be information about time, a qualitative or quantitative information), cleaned or rinsed and the amount of water (or plasma) present in the patient's blood is reduced correspondingly, e.g. according to prescription. In this, the therapy takes usually 3 to 5 hours. The duration may be set in advance. The termination of this period of time may indicate the completion of the blood treatment.

When the blood return ends, the device signals this to the operator in some embodiments. This may be for example the case when the hematocrit present in the extracorporeal blood circuit is reduced (e.g. at a detection device, in particular at a venous substituate/blood detector) to a pre-determined value (e.g. down to 2%).

In some embodiments, the end of the blood treatment is displayed or communicated to the operator. The method follows thereto.

The communication of the end of the blood treatment may be communicated to the operator e.g. by display (e.g. per monitor) and/or per alarm.

The end of the blood treatment may be reached and/or displayed or communicated, when, e.g., the ultrafiltration volume being prescribed or set in advance is removed.

The end of the blood treatment may be reached and/or displayed or communicated, when the end of the treatment is communicated to the operator by means of the user interface.

The end of the blood treatment may be reached and/or displayed or communicated, when alarm systems or alarm limits, which are active during the blood treatment, have been deactivated.

In some embodiments, no blood is withdrawn from the patient during the execution of the method. Therefore the blood treatment is preferably completed prior to beginning the method, and no more blood is introduced into the extracorporeal blood tubing system. Preferably, only blood, which was already treated before the start of the method is reinfused to the patient.

The method begins preferably after the end of the blood treatment, preferably after a delay or immediately after its end.

In some embodiments, the blood pump runs backwards during the execution of method.

"Backwards" may mean that the blood pump conveys in a direction towards the arterial patient connection or towards the arterial patient tube hose.

"Backwards" may mean that the blood pump conveys in a direction, which is opposite to the conveying direction of the blood pump during the blood treatment.

In some embodiments of the method, the blood pump conveys a rinsing liquid which has been connected to the extracorporeal blood circuit for the purpose of blood reinfusion.

In some embodiments of the method, the blood pump conveys saline solution, which is fed into the extracorporeal blood circuit from a bag or another container.

Is some embodiments of the method, the arterial patient line and the venous patient line are connected to each other.

In some embodiments of the method, the arterial patient line and/or the venous patient line are connected, respectively, to a venous section or to an arterial section of the extracorporeal blood circuit or of a blood cassette.

In several exemplary embodiments of the method, the pressure difference between the blood chamber and the spent dialysate chamber of the blood filter is at least partially generated by at least one pump, in particular a conveying device for substitute, an ultrafiltration pump, a substitute pump and/or a blood pump.

In the method, the ultrafiltration pump runs in some embodiments at least temporarily concurrently with the conveying device for substitute, the substitute pump and/or the blood pump. In this way, a pressure difference between the blood chamber and the spent dialysate chamber of the blood filter may be generated in some embodiments.

In certain embodiments, the conveying device for substitute, in particular the blood pump and/or the substitute pump conveys at a flow rate $Q_{conveying\_device}$, $Q_{BP}$ or $Q_{substituate\_pump}$ of between 20 and 300 ml/min, preferably between 30 and 280, between 70 and 240, and particularly preferably between 150 and 210 ml/min.

In some embodiments, the ultrafiltration pump conveys preferably at a fraction of the flow rate of the conveying device for substitute, in particular of the blood pump and/or of the substitute pump, such that the quotient $Q_{UF}/Q_{conveying\_device}$, $Q_{UF}/Q_{BP}$ or $Q_{UF}/Q_{substituate\_pump}$ is preferably in a value range between 0.005 to 0.9 or between 0.01 to 0.8, particularly preferably, between 0.1 to 0.7 and most preferably between 0.2 to 0.6. In this, Qui is preferably between 1 and 80 ml/min.

In some embodiments of the method, the ultrafiltration pump conveys preferably between 1 ml/min and 150 ml/min, particularly preferably between 15 ml/min and 150 ml/min.

In some embodiments of the method, the ultrafiltration pump conveys preferably between 15 ml/min and 150 ml/min, particularly preferably between 20 ml/min and 150 ml/min.

In some embodiments of the method, the ultrafiltration pump conveys preferably above 15 ml/min, particularly preferably above 20 ml/min. This may advantageously accelerate the reinfusion. In addition, the mixing of substituate and blood may in this way be advantageously limited to a short or shorter length of tubing when compared to the prior art.

In some embodiments of the method, the conveying rates given herein are at least temporarily reached.

In some embodiments, the flow rate or the quotient $Q_{conveying\_device}$, $Q_{UF}$ and/or $Q_{BP}$ is automatically controlled or regulated by the device.

In some embodiments, $Q_{UF}/Q_{conveying\_device}$, $Q_{UF}/Q_{BP}$ or $Q_{UF}/Q_{substituate\_pump}$ is set, at the beginning of the return, low or lower than at a later time, since the hematocrit of the liquid in the filter is usually still high and a comparatively strong increase in viscosity or hematocrit should be avoided. In further course, the quotient is preferably increased, since the hematocrit of the liquid in the filter has typically decreased in the meantime. The hematocrit of blood/substituate mixture is preferably increased through the method so that the patient is advantageously infused with as little substituate as possible.

In some embodiments, $Q_{UF}/Q_{conveying\_device}$, $Q_{UF}/Q_{BP}$ and/or $Q_{UF}/Q_{substituate\_pump}$ increases with increasing infused volume of substituate. The increase occurs preferably monotonically, particularly preferably strictly monotonically. The following table indicates for an embodiment the exemplary connection between $Q_{UF}/Q_{BP}$ for a volume of the extracorporeal circuit of about 200 ml.

| Introduced substituate volume $V_{substituate}$ [ml], cumulative | $Q_{UF}/Q_{BP}$ |
|---|---|
| 0 | e.g. 0.1; typically: 0.01 to 0.3 |
| 40 | e.g. 0.1; typically: 0.01 to 0.3 |
| 80 | e.g. 0.3; typically: 0.1 to 0.5 |
| 120 | e.g. 0.5; typically: 0.1 to 0.7 |
| 160 | e.g. 0.6; typically: 0.3 to 0.8 |
| 200 | e.g. 0.7; typically: 0.5 to 0.8 |
| 240 | e.g. 0.7; typically: 0.5 to 0.8 |
| 280 | e.g. 0.7; typically: 0.5 to 0.8 |

In an embodiment of the method, the desired flow rate of the substituate is adjustable by the operator. The flow to the patient ($Q_{patient}$) is preferably set according to or follows the following rule: $Q_{patient} = Q_{conveying\_device} - Q_{UF}$, in particular $Q_{patient} = Q_{BP} - Q_{UF}$, wherein the blood pump has been herein only exemplarily considered as the sole conveying pump for substituate.

In some embodiments of the method, the desired flow into the patient ($Q_{PatientDesired}$) is adjustable by the operator and the device calculates, e.g., recurringly or continuously, $Q_{conveying\_device}$ or $Q_{BP}$ according to the rule:

$$Q_{conveying\_device} = Q_{PatientDesired} + Q_{UF},$$

in particular $Q_{BP} = Q_{PatientDesired} + Q_{UF}$.

In some embodiments of the method, $Q_{UF}/Q_{conveying\_device}$, $Q_{UF}/Q_{BP}$ and/or $Q_{UF}/Q_{substituate\_pump}$ is controlled (e.g. in the sense of a rising ramp) depending on the amount of substituate conveyed so far.

In some embodiments of the method, $Q_{UF}/Q_{conveying\_device}$, $Q_{UF}/Q_{BP}$ and/or $Q_{UF}/Q_{substituate\_device}$ is controlled (rising ramp) depending on the amount of the substituate already conveyed and on the volume of the extracorporeal blood circuit known e.g. from the filling of the system. For example, $Q_{UF}/Q_{conveying\_device}$ of the conveyed substituate increases monotonically, preferably strictly monotonically. $Q_{UF}/Q_{conveying\_device}$ is, particularly preferably, proportional to the already-conveyed substituate volume.

In some embodiments of the method, $Q_{UF}/Q_{conveying\_device}$, $Q_{UF}/Q_{BP}$ and/or $Q_{UF}/Q_{substituate\_pump}$ is individually controlled depending on a prescription or on acute requirements of the patient.

In some embodiments of the method, the $Q_{UF}/Q_{conveying\_device}$, $Q_{UF}/Q_{BP}$ and/or $Q_{UF}/Q_{substituate\_pump}$ is varied during the execution of the method, e.g., in order to regulate the hematocrit, e.g., in the venous blood line to a pre-determined value.

In some embodiments of the method, $Q_{UF}/Q_{conveying\_device}$, $Q_{UF}/Q_{BP}$ and/or $Q_{UF}/Q_{substituate\_pump}$ is varied in order to regulate the hematocrit in the extracorporeal blood circuit to a desired value (typically between 30 and 60%). For example, the flow pressure of the filter on the blood side may be used as the input value of the regulator (e.g. $P_{filter\_longitudinal}$=pre-filter(post pump)pressure–post-filter(venous)pressure, i.e. the pressure which prevails between pump and filter entry, minus the pressure which is present in the venous line downstream of the filter). In this, the flow resistance is proportional to the viscosity of the liquid in the extracorporeal blood circuit. The viscosity is proportional to the hematocrit of the blood in the filter.

In some embodiments of the method, $Q_{UF}/Q_{conveying\_device}$, $Q_{UF}/Q_{BP}$ and/or $Q_{UF}/Q_{substituate\_pump}$ is regulated depending on the hematocrit, for example in the venous blood line, which hematocrit is determined by means of the detection device, in particular by means of the venous substituate/blood detector and depending on a pre-determined substituate volume to be conserved. For example, the operator specifies an amount of substituate to be conserved as compared to the prior art and $Q_{UF}/Q_{conveying\_device}$, $Q_{UF}/Q_{BP}$ and/or $Q_{UF}/Q_{substituate\_pump}$ is varied or regulated depending on the hematocrit of the liquid, e.g. in the venous patient line (e.g. detected by an optical detector, e.g. a venous substituate/blood detector).

In some embodiments of the method, $Q_{UF}/Q_{conveying\_device}$, $Q_{UF}/Q_{BP}$ and/or $Q_{UF}/Q_{substituate\_pump}$ is set, in the case of simultaneous arterial and venous reinfusion, depending on the hematocrit of the liquid in the arterial patient line such that the hematocrit of the liquid, which flows through the venous patient line into the patient, is comparatively very high (e.g. >50%, preferably >55%, particularly preferably about 60%). For example, the liquid from the arterial patient line having a comparatively low hematocrit (e.g. 10%) may mix, when reinfused into the patient's vascular system, with the liquid from the venous patient line having a high hematocrit (e.g. 60%) such that a hematocrit results in the patient's vascular system with a value (e.g. <60%), which lies between the values for the hematocrit in the venous or the arterial patient line. In this way, a particularly low reinfusion of substrate may be advantageously achieved in some embodiments.

In some embodiments of the method, $Q_{UF}/Q_{conveying\_device}$, $Q_{UF}/Q_{BP}$ and/or $Q_{UF}/Q_{substituate\_pump}$ is set such that together with the amount of water which is removed from the blood already prior to the blood return (during the actual treatment) the value of the prescription results.

In some embodiments, the method may advantageously be used in any known reinfusion method (e.g. NaCl, online, online simultaneously etc.).

In some embodiments, the method serves to partially, in others to completely, remove blood from a blood filter and/or blood circuit used for the blood treatment of a patient after completion of the blood treatment session.

The utilized blood filter is in some embodiments a hemodialyzer or a hemofilter.

The membrane arranged between the blood chamber and the spent dialysate chamber is in certain embodiments a semi-permeable membrane.

In specific embodiments, the venous blood line leads from the blood chamber of the blood filter to a venous blood chamber (herein also denoted as venous air separation chamber) and/or a venous connection point or connection device.

In certain exemplary embodiments, the arterial blood line leads from an arterial connection point or connection device to the blood chamber of the blood filter.

In some exemplary embodiments, the control and/or regulating device is configured to effect in interaction with a medical blood treatment apparatus a blood treatment (not) and a subsequent displacement of the blood from the blood chamber by means of the introduced substituate.

In specific exemplary embodiments, the medical treatment apparatus and/or the blood filter is connected to a blood cassette.

In some embodiments of the method, the method encompasses detecting a qualitative change of the content of the conduit interior of the extracorporeal blood circuit.

In some embodiments of the method, a predetermined amount of substituate is introduced into the conduit interior of the extracorporeal blood circuit by operating a conveying device, for example the blood pump, the substituate pump or the fresh dialysis liquid pump.

In some particular embodiments of the method, a substituate (alternatively denoted as substituate liquid) or fresh dialysis liquid is conveyed until the detection device detects a substituate, in a predetermined degree (e.g. amount or concentration), in the conduit interior of the extracorporeal blood circuit.

In some embodiments of the method, the detection device is arranged with a predetermined distance to a venous access device. In these embodiments, the method further encompasses conveying the content of the conduit interior of the extracorporeal blood circuit across the predetermined distance to the venous access device after dialysate has been detected at or by the detection device.

In certain embodiments of the method, blood contained in the conduit interior of the extracorporeal blood circuit is introduced into the vascular system of the patient via the venous access device.

In some embodiments, the method further encompasses introducing air into the extracorporeal blood circuit, for example after completion of a blood treatment session and/or after the partial or complete removal of blood from the extracorporeal blood circuit.

A "blood treatment session" may be, for example, a treatment unit comprising hemodialysis, hemofiltration, hemodiafiltration and/or a cell separation method and it is directed to the treatment and/or purification of blood. For performing such a blood treatment, a suitable blood treatment apparatus is used.

A blood treatment apparatus which is suitable for executing the method comprises, or is connected to, in some embodiments optionally an extracorporeal blood circuit having a conduit interior, at least one conveying device for introducing and/or conveying at least two fluids in the conduit interior of the extracorporeal blood circuit, and for example a device for treating the blood of the patient, such as one or several blood filters and/or one or several dialyzers and/or one or several adsorbents. It may further comprise containers for storing fluids, elements for introducing the fluids, such as for example tube elements and/or valves, as well as further devices, such as for example an air separation chamber or bubble trap for removing air from the blood during the blood treatment and/or sensors and/or detectors for detecting various relevant parameters, such as for example a pressure in the extracorporeal blood circuit.

Conveying devices, as mentioned herein, include membrane pumps, tube pumps, roller pumps, and so on. The blood pump, a substituate pump and/or a fresh dialysis liquid pump may be embodied, e.g., as a tube pump or a roller pump. However, also a different type of pump may be used, e.g. a membrane pump.

A conveying device for fresh dialysis liquid or substituate may be a "second" conveying device, i.e. a conveying device, which is not identical to the blood pump. The blood pump may, however, also be designed such that it both executes the function which is typical for a blood pump as well as is able to perform the function of introducing substituate into the conduit interior and/or conveying the conduit content. Whenever a conveying device for substituate is mentioned herein, this relates, just for the purpose of better readability, to the blood pump or to a conveying device different from the latter. Both versions are equally encompassed by the present invention.

The method encompasses, in certain embodiments, the step of introducing air into the conduit interior of the extracorporeal blood circuit for emptying it from fluid, e.g., by operating the blood pump. The air may for example be atmospheric air. The present invention is, however, not intended to be limited to the sole use of air, rather to include all gaseous fluids in addition to air, which are suitable for the purposes of the present invention.

Introducing air into the conduit interior of the extracorporeal blood circuit after completing the blood treatment session may occur exclusively or may be supported by means of the blood pump, by means of the second conveying device or by means of a compressed air source.

Combinations of the aforementioned options are also encompassed by the present invention, as well as a passive admission of air.

Introducing substitute into the conduit interior of the extracorporeal blood circuit takes place, as described above, in some particular embodiments by operating the conveying device for substitute, in particular the blood pump and/or the substitute pump.

The blood pump may convey substitute by drawing it from a supply line to a container for the substitute, wherein the supply line enters into the extracorporeal blood circuit upstream of the suction side of the blood pump. For this, e.g., an outlet with a tube clamp, which is provided in the arterial branch of the extracorporeal blood circuit, may be provided.

If it is intended that the blood pump introduces and conveys both blood and substitute into the extracorporeal blood circuit, the method may be executed with just one pump. Even though such a further preferred embodiment is encompassed by the present invention, embodiments, in which a blood pump and a second conveying device are used, are described in the following. The following description is intended to simplify the understanding of the principles and functions of the individual components underlying the present invention. Preferably, the method is executed with the help of a UF pump, which may generate negative pressure in the spent dialysate chamber.

In a further preferred embodiment, detecting a qualitative change of the content of the conduit interior of the extracorporeal blood circuit by means of at least one detection device, which is arranged in or at a section of the extracorporeal blood circuit, is encompassed.

The "qualitative change" may relate to one or several areas or sections of the extracorporeal blood circuit, for example an area or section in which the detection device is arranged.

"A qualitative change of the content of the conduit interior" includes a change in the composition of the content of the conduit interior, such as for example a change of the individual parts of blood and/or substitute in the conduit interior or a section thereof, in relation to each other. Also, the lack of a fluid which was previously present may represent a change in the composition. A qualitative change may also be a transition from blood to substitute. Such changes may for example be easily detected because of an optical change of the content, such as a brightening or darkening of the content or a color change, e.g., an alteration to red or an increase of the red tone.

The "detection device" which is arranged in a section of the extracorporeal blood circuit may for example be an optical sensor, which detects an optical change of the content of the conduit interior or a property of its content. Further suitable sensors include pressure sensors, conductivity sensors and sensors for detecting a change in the density of the content of the conduit interior of the extracorporeal blood circuit, without being limited thereto. In some embodiments, a detection device is, or comprises, a substitute/blood detector.

The "section of the extracorporeal blood circuit" may be an arterial and/or venous section of the extracorporeal blood circuit. The "arterial section" relates to a section of the extracorporeal blood circuit through which blood flows from the vascular system of the patient in the direction towards the blood treatment device or towards the blood filter. The "venous section" refers to the section of the extracorporeal blood circuit through which the blood from the blood treatment device or from the blood filter flows back to the vascular system of the patient.

In another preferred embodiment of the method, the extracorporeal blood circuit encompasses at least one access device which is connectable with a section of the vascular system of the patient, and the method encompasses disconnecting the extracorporeal blood circuit from the vascular system of the patient, in particular in the area of a first, for example arterial, access device, in particular at an end of the extracorporeal blood circuit.

Disconnecting the extracorporeal blood circuit from the vascular system of the patient includes interrupting a connection between the extracorporeal blood circuit and the vascular system of the patient in a section of the extracorporeal blood circuit, for example at an end thereof. In doing so, the interruption may take place both at the arterial and at the venous section, wherein in disconnecting the arterial section of the extracorporeal blood circuit is preferred.

Disconnecting in the "area of the first access device" may be understood as for example pulling out the arterial connection needle of a double-needle access.

Disconnecting may also be understood as interrupting the flow connection between the arterial section of the extracorporeal blood circuit and the arterial connection needle.

In the case of the single-needle version, disconnecting may be understood as interrupting the connection between the arterial leg of the "Y"-shaped section of the extracorporeal blood circuit and the only connection needle, which is connected to the vascular system of the patient. The open lumen of the arterial leg of the Y-part may be closed in any manner (manually, machine-induced, automatically and so on) after being separated.

Alternatively or in addition, the same may be also applied to the venous section of the extracorporeal blood circuit and the venous access to the vascular system of the patient.

An "addition point for the extracorporeal blood circuit for substitute into the line interior of the extracorporeal blood circuit" may be arranged in the arterial and/or the venous section of the extracorporeal blood circuit. It is preferred that the "addition point" is arranged in a section of the extracorporeal blood circuit, which is perfused upstream of the blood treatment device, as well as for example upstream of the blood filter.

Suitable examples for an addition point include an opening/closing valve, a stopcock, a connectable branch line of a branched section of the extracorporeal blood circuit and so on.

A "pre-determined substitute amount or fresh dialysis liquid amount" may correspond to a certain feed volume and/or a certain path length of the line interior of the extracorporeal blood circuit along which path the content is conveyed and can, for example, be produced by operating a membrane pump.

The substitute amount or the fresh dialysis liquid amount may preferably be pre-determined as a parameter, for example as a volume with a preset value and unit. The absolute amount of the substitute may preferably be stored and/or enterable for example in a control device of the treatment apparatus. The substitute amount may preferably be conveyed precisely within the limits of the technical precision.

In order to pre-determine an exact amount of substitute, e.g., technical specifications of the utilized extracorporeal blood circuit, such as for example the inner volumes of the tube set, may be stored in, or entered into the control device. By means of the technical specifications of the individual components of the extracorporeal blood circuit, for example a required feed time and/or a feed volume may be calculated.

A "limited amount of substitute or fresh dialysis liquid" may be for example an amount of substitute liquid, which was chosen according to the operating personnel's empirical values. Preferably, a limited amount of fluid may be introduced and conveyed for so long until substitute is detected in the conduit interior of the extracorporeal blood circuit at a further detection device. A limited substitute amount thus does not have to be exactly known and/or to correspond to a certain feed volume. A limited amount of substitute may, however, be indirectly limited by the inner volume of the components of the extracorporeal blood circuit through which the substitute amount flows, in particular the inner volume of the section between the addition point for substitute and/or the blood treatment device and a further detection device. In this way, the volume is thus determined in the sense of "limited", however, without being exactly known, and without being expressible for example in milliliters and/or without having been stored or being enterable in a controller. Introducing a limited amount of substitute may be of advantage, e.g., if the type of the filter of a blood treatment device or its capacity is unknown or incorrectly stated.

In doing so, the substitute may be introduced from a provided storage container into the extracorporeal blood circuit at the addition point for the substitute via corresponding conduit systems of the extracorporeal blood circuit.

The "detection device" is defined as above and may be arranged for example in the venous section of the extracorporeal blood circuit, e.g., between the blood treatment device and the venous access device to the vascular system of the patient and in particular between a drip chamber in the venous section and the venous access device.

The detection device may detect the occurrence of substitute in a certain section of the conduit interior of the extracorporeal blood circuit, for example by means of an optical change of the content of the line interior.

If the detection device detects the presence of air or substitute in the conduit interior of the extracorporeal blood circuit, conveying the "substituate/blood content" may be stopped.

This may take place by stopping the respective conveying device.

Further, in another embodiment of the method it is preferred to arrange the detection device with a predefined distance to a second access device and to convey the content of the line interior along the predefined distance to the access device after substitute or a pre-determined transmission or light transmission, a pre-determined color shade or a pre-determined change of color has been recognized at the detection device.

In a further preferred embodiment of the method, the blood contained in the conduit interior of the extracorporeal blood circuit is returned into the vascular system of the patient—in particular substantially completely—via the second access device. The term "substantially completely returned" means herein that the blood present in the conduit interior of the extracorporeal blood circuit is removed nearly without any remaining substance from the extracorporeal blood circuit. The blood residues possibly remaining in the extracorporeal blood circuit for technical reasons such as wetting behavior or the blood residues remaining in the drip chamber are herein to be regarded as negligibly small.

"Returning blood into the vascular system of the patient" may take place if or when an end of the extracorporeal blood circuit, such as for example the end of the venous section, e.g., the venous connection needle, is connected to the vascular system of the patient. This connection may be maintained or re-established after the completion of the blood treatment session.

Due to the fact that the method as described herein is executable with the treatment apparatus, it is referred to the respective embodiments as described herein in order to avoid repetition.

A development of the treatment apparatus provides the arrangement of at least one detection device for detecting at least one change of the content of the conduit interior of the extracorporeal blood circuit or one property of the content in a section of the extracorporeal blood circuit. A property of the content may be a composition, a physical, chemical, or biological parameter, for example an optical density, a pH value and much more suchlike. Such a detection device may correspond to the one described above, thus it is referred to its above description in order to avoid repetition.

A treatment apparatus may, without being limited thereto, be suitable and/or configured to perform hemodialysis, hemofiltration, hemodiafiltration, and/or separation methods.

One or more of the herein-mentioned advantages may be achievable via some embodiments.

In some embodiments, the method is changed or modified as compared to the prior art so that during the reinfusion procedure through the filter, water is removed from blood/blood mixture that resulted from displacing the blood by substituate. Due to this, the blood/substitute mixture, which leaves the filter towards the patient, contains in some embodiments less substitute.

The net water, which is removed in the entire treatment (including reinfusion), is usually an important treatment parameter for a patient with renal insufficiency. In order to remove a certain net amount of water from the patient's blood throughout the entire treatment, the water, which in addition to blood, has also necessarily been infused during the reinfusion, is usually already removed from the patient's blood in the course of the treatment before.

As the amount of water, which is removed in the actual treatment from the patient's blood, increases, and the strain on the circulation of the patient increases often considerably. This often leads to physiological problems during the treatment. The amount of liquid, which is infused during the reinfusion and which as described supra has been removed prior to completing the treatment, often leads to physiological problems as well. In some embodiments, such physiological problems may be advantageously prevented or diminished.

The method may entail in some embodiments one, several, or all of the aforementioned or following advantages:
  Reduced portion of substitute in the blood/substitute mixture, which is infused into the patient during the reinfusion. In this, the amount of water to be removed during the treatment preceding the method may be reduced.

improved circulation stability of the patient (in particular for pediatric patients)

reduced amount of the vascular total liquid intake during the reinfusion reduced duration of the reinfusion procedure cost saving Reduced blood loss by the patient through less residual blood, which in the prior art remains in the extracorporeal blood circuit after the reinfusion. In the prior art, it is often a question whether the blood return should be accomplished as completely as possible, whereby a lot of substituate is infused, or whether as little as possible substituate should be infused, which is associated with a less efficient blood return and thus with a blood loss of the patient. The method avoids these disadvantages in some embodiments.

reduced anemia in dialysis patients reduced need for drugs that aid blood formation (e.g. erythropoietin)

increasing the patient's wellbeing reduction of the effective treatment time (dialysis) during the reinfusion and corresponding reduction of the dialysis time (with corresponding cost saving) and/or improved clearance Some embodiments advantageously reduce the substituate amount, which is infused together with the blood during the reinfusion.

Thus, some embodiments may contribute to improving the effectiveness of the arterio-venous blood return, that is to say the simultaneous reinfusion both via the arterial and via the venous patient connection.

Since the method may be executed directly after a blood treatment session has come to an end, it is simply and easily executable and does not require any technically complex, time- and/or cost-intensive steps.

The method may advantageously preferably be executed with the substituate, which is used or present anyway in a blood treatment or with a liquid which is used or present anyway in a blood treatment, such as for example an isotonic saline solution, e.g., a 0.9% NaCl solution. This in turn advantageously contributes to saving costs and time.

Further, the method may enable a removal of blood from the arterial section of the extracorporeal blood circuit and in particular from the arterial connection needle and the return of the blood into the vascular system of the patient. The step in reinfusion methods of the prior art by which the blood present in the arterial connection needle is pushed out in the retrograde, with the aid of, e.g., a syringe, which is filled with saline solution, may thus advantageously be avoided.

The method may thus offer the advantage of essentially completely recovering the blood present in the conduit interior of an extracorporeal blood circuit after its use for a blood treatment for the patient.

The procedure may ensure that no air enters the vascular system of the patient during emptying. Furthermore, in some embodiments of the method no foaming in the area of a blood filter present in the extracorporeal blood circuit can occur, which would hamper emptying the blood from the extracorporeal blood circuit. However, blood remaining in the blood filter or in the extracorporeal blood circuit constitutes a contamination risk.

BRIEF DESCRIPTION OF THE DRAWINGS

Hereafter, the method is explained based on preferred embodiments thereof with reference to the accompanying drawings in which the following applies.

DETAILED DESCRIPTION OF THE FIGURES

After completion of a blood treatment session, the blood or blood mixture in the extracorporeal blood circuit (and in particular in the blood filter) is typically returned to the patient. This usually takes place by introducing substituate into the extracorporeal blood circuit, whereby the blood present therein is displaced downstream and, thus, is reinfused into the patient, e.g. through the venous patient connection.

Usually, in the prior art, a diffuse transition region from blood to substituate develops, in which blood is mixed with substituate. The blood/substituate mixture present in flow direction after the blood filter (post-filter) contains, thus, often substituate. Undesirably, a lot of substituate is needed for rinsing the extracorporeal blood circuit all the way to the venous patient connection. Some of this substituate is moreover supplied to the patient, which is usually not desired, particularly for dialysis patients after completion of the blood treatment.

Figure 1:
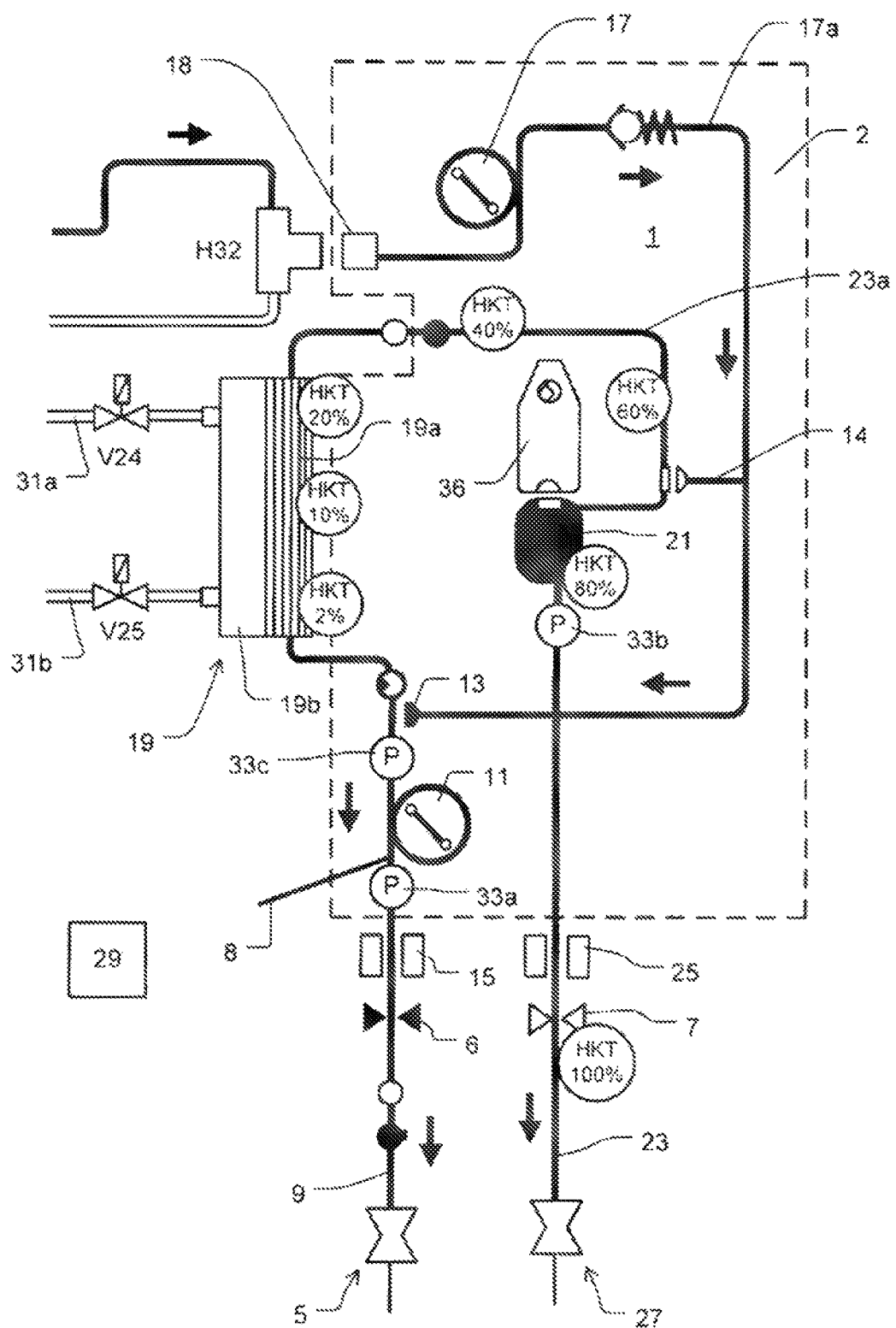
FIG. 1 shows, schematically simplified, the execution of a method from the prior art by means of a known medical treatment device.
Figure 2:
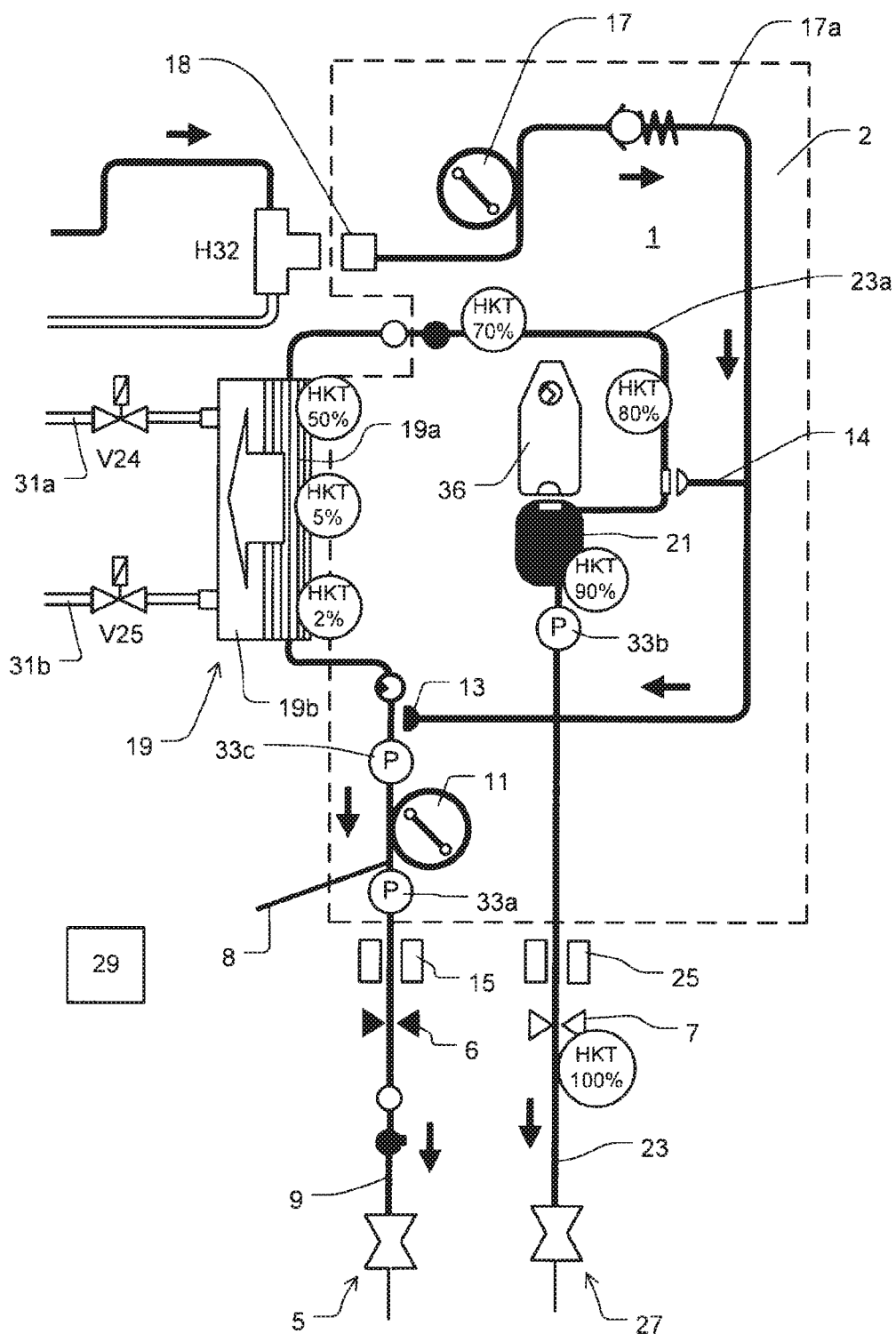
FIG. 2 shows, schematically simplified, an exemplary embodiment of a medical treatment apparatus while executing an example method disclosed herein.

A conventional method is depicted in FIG. 1, and a new method according to the present disclosure is depicted in FIG. 2 for removing blood and/or a blood mixture, after completion of the treatment session, from a blood filter 19 used for the blood treatment of a patient. In this, one example, each, with a simultaneous reinfusion (also referred to as online closed circuit) and residual blood distribution after conveying half of the conventional amount of reinfusion (e.g. about 200 ml) is shown schematically in snapshots.

FIG. 1 shows an extracorporeal blood circuit 1, which is connected or connectable via a double needle access to the vascular system of the patient (not shown). The blood circuit 1 is disposed optionally in sections thereof in or on a blood cassette 2. It is connected to a blood treatment apparatus 4. Controlling or regulating the blood treatment apparatus 4 may be carried out by a control or regulating unit 29.

The extracorporeal blood circuit 1 comprises an arterial patient hose tube 6 and an arterial connection needle 5 (as an example of an access device) of an arterial section 9 or of an arterial patient line or blood line 9. The extracorporeal blood circuit 1 further comprises a venous patient tube clamp 7 and a connection needle 27 (as an example of a further or second access device) of a venous section 23 or of a venous patient line or blood line 23.

A blood pump 11 is provided in the arterial section 9. A substituate pump 17 is connected to a substituate line 17a. The substituate line 17a may be connected to a substituate source via a, preferably automatic and optional substituate port 18, herein shown as not connected. By means of the substituate pump 17, substituate may be introduced via pre-dilution or via post-dilution through associated lines 13 or 14 into line sections, e.g., into the arterial section 9 or into a venous section 23a (between the blood chamber 19a and an optional single needle chamber 36) of the extracorporeal blood circuit 1.

A blood filter 19 is provided in the blood circuit 1. The blood filter 19 comprises the blood chamber 19a which is connected to the arterial section 9 and to the venous section 23. A spent dialysate chamber 19b of the blood filter 19 is connected to a fresh dialysate inlet line 31a, which leads to the spent dialysate chamber 19b and to a spent dialysate outlet line 31b which leads away from the spent dialysate chamber 19b.

The fresh dialysate inlet line 31a optionally comprises a valve V24 by means of which the flow within the fresh dialysate inlet line 31a may be stopped. The spent dialysate outlet line 31b optionally comprises a valve V25 by means of which the flow within the spent dialysate outlet line 31b may be stopped.

The fresh dialysate inlet line 31a is further optionally connected to a compressed air source 26 (not shown here, see however FIG. 3) by means of another internal valve of the device. The compressed air source 26 may be provided as a part or component of the treatment apparatus 4 or may be a separate part therefrom. A pressure sensor 37 (herein not shown, see however FIG. 3) may be provided downstream of the compressed air source 26.

The arrangement of FIG. 1 encompasses an optional, arterial detector 15 for detecting air and/or blood. The arrangement of FIG. 1 further encompasses one, two or more pressure sensor(s) 33a, 33b, 33c, e.g. at the points shown in FIGS. 1 and 2. In order to empty the blood chamber 19a of the blood filter 19 from blood after the treatment, substitute may be added in pre-dilution to the blood circuit 1 and to the blood chamber 19a, as shown in FIG. 1, by the substitute pump 17 through the addition site 13.

Alternatively or in addition, the substitute may be introduced without operating or not by exclusive operation of the substitute pump 17, but rather by (exclusively or additionally) operating the blood pump 11. To this end, the arterial patient hose 6 clamp is closed and substitute is introduced into the extracorporeal blood circuit 1 via a supply line 8 from a storage container for the substitute.

The substitute/blood content, thus produced, is conveyed along the conduit interior of the extracorporeal blood circuit 1 by operating the blood pump 11 and/or the substitute pump 17. The substitute/blood content is pressed or conveyed through the blood filter 19, a venous air separation chamber 21, and the venous section 23 of the extracorporeal blood circuit 1 in order to remove the blood from the extracorporeal blood circuit 1 in the direction towards the venous connection needle 27, from the blood filter 19.

A venous substitute-blood detector 25 is optionally arranged in the venous section 23 of the extracorporeal blood circuit 1 as an example of a detection device, which detects the presence of substitute at a predetermined position of the conduit interior of the extracorporeal blood circuit 1. The blood pump 11 and/or the substitute pump 17 optionally continues conveying the substitute/blood content until the blood, which was present in the venous section 23 of the extracorporeal blood circuit 1, is removed from it and returned to the vascular system of the patient via the venous connection needle 27, and/or until the presence of substitute (or the decrease of the hematocrit in the conduit interior, for example down to 2%) is detected in the conduit interior at the venous substitute/blood detector 25. The conveying operation of all pumps may be stopped at this point. An optical and/or acoustical signal may be output.

FIG. 1 shows a distribution of residual blood after conveying half of the amount of the reinfusion fluid, which is conventionally required for removing blood from the blood tubing circuit 1. The hematocrit HKT at the venous substituate/blood detector 25 amounts to, at the point in time represented in FIG. 1, 100% of the original HKT value present in the extracorporeal blood circuit 1 immediately before the completion of the blood treatment method. The hematocrit HKT at the venous substitute/blood detector 25 is thus the original HKT value in the extracorporeal blood circuit 1 immediately before the completion of the blood treatment method. Therefore, the hematocrit HKT is given in FIG. 1 as "HKT 100%" at the venous substitute/blood detector 25. It is important to know that all of the percentage values concerning HKT in FIG. 1 and in FIG. 2 are relative values: The percentage values given at the indicated points of the blood tubing circuit 1 indicate which fraction the HKT measurable at those points represents relative to the HKT present in the conduit interior at the end of the treatment.

The hematocrit HKT of the blood present in the extracorporeal blood circuit 1 is described with HKT and a percentage value at the various points in FIG. 1. The percentage describes the relation of the current hematocrit HKT at the indicated points to the original hematocrit HKT present in the extracorporeal blood circuit 1 immediately before completion of the blood treatment method. If for example the hematocrit HKT in the extracorporeal blood circuit 1 is 42% before the completion of the blood treatment, then "HKT 100%" means that the hematocrit HKT is still at 42%.

By infusing substitute using the substitute pump 17 through the addition site 13 for pre-dilution, a mixture in the extracorporeal blood circuit 1 occurs or develops at the transition from substitute to blood, in particular in the blood filter 19, which mixture influences the measurable HKT.

In FIG. 1, the hematocrit HKT at the entry of the blood chamber 19a of the blood filter 19 is 2% of the original value. The hematocrit HKT increases across the blood chamber 19a—initially to 10% and then at the venous end of the blood chamber 19a to 20% of the original measurable value. In the venous section 23, the hematocrit HKT further increases first to first 40% shortly after the blood filter 19, then to 60% in section 23a, to 80% after the air separation chamber 21 up to 100% at the venous substituate/blood detector 25 (in both FIG. 1 and FIG. 2. the indicated percentages refer to the ratio of the currently present hematocrit HKT to the original hematocrit HKT, see supra, and are thus relative values). It is now clear that in the prior art the mixing of substitute and blood takes place over a longer distance, such that a substantial volume of substitute must be infused for achieving a complete or an almost complete reinfusion of blood.

The method illustrated in a snapshot in FIG. 2—just as in FIG. 1—shows a residual blood distribution after conveying half of the fluid, which is conventionally reinfused. Unlike FIG. 1, there is a pressure difference in the blood filter 19 with a lower pressure in the spent dialysate chamber 19b and a higher pressure in the blood chamber 19a. The pressure difference may be e.g. created by generating an absolute or a relative negative pressure in the spent dialysate chamber 19b of the blood filter 19, e.g. by removing liquid from the spent dialysate chamber 19b through the valve V25 by means of an ultrafiltration pump (UF-pump 40, not shown, see FIG. 3). The pressure difference may be generated alternatively or additionally through a flow resistance downstream of the blood chamber 19a, e.g. in the venous section 23a, if at the same time fresh dialysis liquid is introduced into the blood chamber 19a, e.g. by means of the substituate pump 17 and/or the blood pump 11.

By means of the pressure difference, the liquid is removed from the extracorporeal blood circuit 1 (see arrow in the blood filter 19). This means that the hematocrit HKT in the extracorporeal blood circuit 1 is during the blood return generally or at times higher than in FIG. 1. This is seen at the blood filter 19, at the entry of which, just like in FIG. 1, a hematocrit HKT of 2% (of the original value) may be observed. At the exit of the filter 19, the hematocrit HKT is already 50% compared to 20% (of the original value, respectively) in the method shown in FIG. 1. This is due to the fact that water has been removed from the blood/substituate mixture in the blood filter 19.

At the points in FIG. 1, at which the hematocrit HKT is 40%, 60% and 80%, it is 70%, 80%, or 90% in FIG. 2. The transition from blood to substituate is thus sharper than in the conventional method of FIG. 1. Less substituate is required for flushing all the way to the venous patient connection. Furthermore, the blood/substituate mixture downstream of the filter 19 contains comparatively less substituate.

Figure 3:
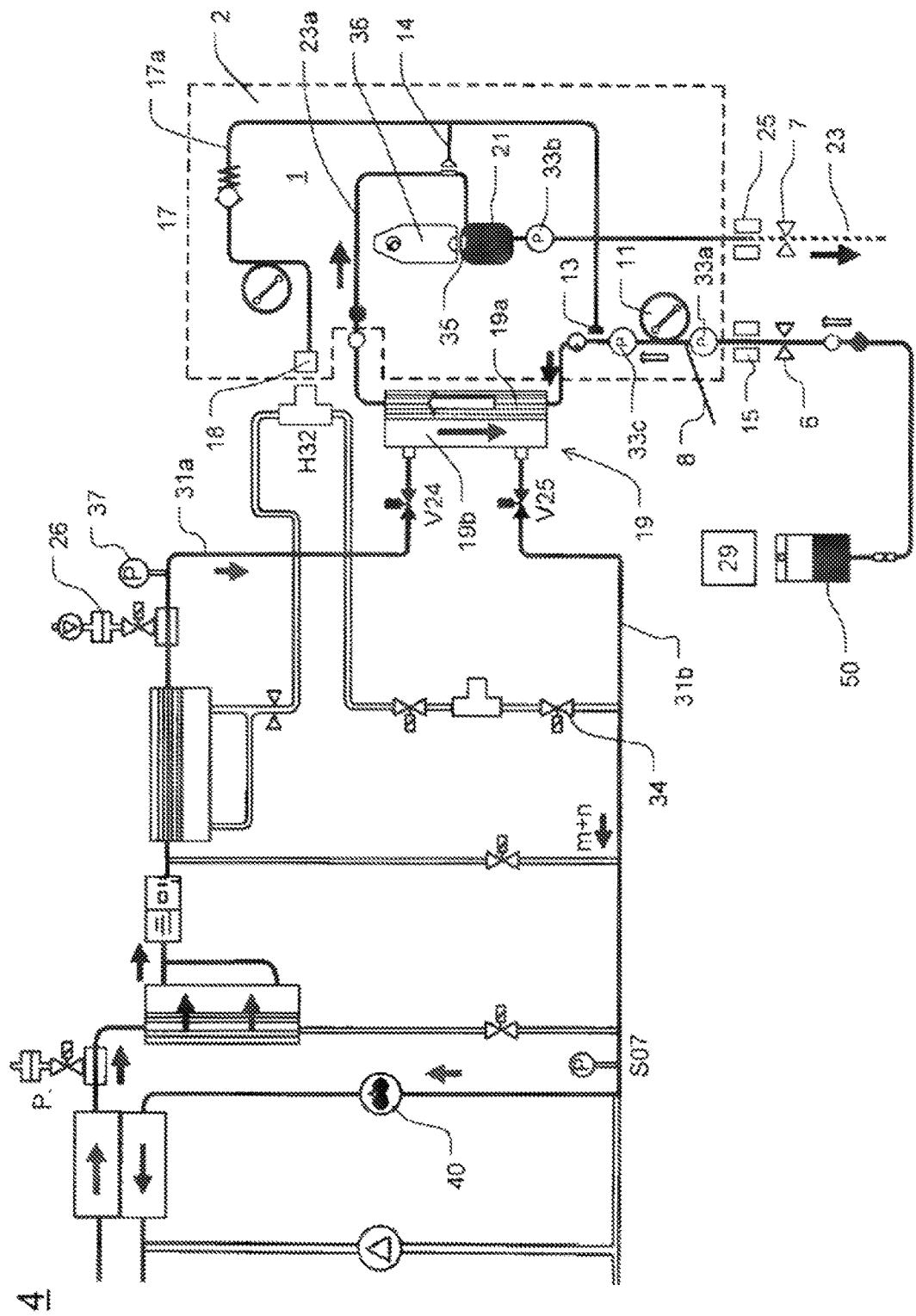
FIG. 3 shows a further method from the prior art, executed by a known medical treatment device.

FIG. 3 shows an exemplary device behavior during a blood return known from the prior art. A bag 50 containing physiological saline, which is placed at the arterial section 9 is a source for substituate with which the blood is displaced out of the extracorporeal blood circuit 1. Unlike FIGS. 1 and 2, the substituate is conveyed into the blood filter 19 with the aid of a blood pump 11.

To this end, no patient blood is cleaned in the blood filter 19, the spent dialysate chamber 19b and the membrane of the blood filter 19 are not perfused anymore so that the amount of water (plasma) in the patient blood is not reduced any further. Hence, the flow rate of the blood pump 11 reaches the patient (the flow rate is e.g. 30 to 200 ml/min). The valves V24 and V25 are both closed, and the UF pump 40 is switched off. The arterial blood pump 11 conveys NaCl solution into the extracorporeal blood circuit 1. In this, the flow rate is e.g. 30 to 200 ml/min.

The device behavior during the blood return in an exemplary embodiment may also be illustrated with reference to FIG. 3. The spent dialysate chamber 19b is optionally not perfused anymore in an embodiment, i.e., there is no flow, except through the membrane, into the spent dialysate chamber. The amount of water (the plasma fraction) of the patient blood is further reduced. In this, the valve V24 is closed and the valve V25 is open. The UF pump 40 is switched on and pumps at e.g. 1 to 80 ml/min to generate a negative pressure in the spent dialysate chamber 19b and thereby to remove water from the blood chamber 19a across the membrane. The arterial blood pump 11 conveys here for example NaCl solution from the bag at the arterial section 9 into the extracorporeal blood circuit 1 at a flow rate of e.g. 30 to 280 ml/min.

The flow rate within the extracorporeal blood circuit 1 across the membrane of the filter 19 to the treatment apparatus 4 is in this example, equal to the conveying rate of the UF pump 40. The flow rate that reaches the patient is in this example, the flow rate conveyed by the arterial pump minus the flow rate conveyed by the UF pump. The flow rate into the vascular system of the patient (the sum of arterial and venous flow rates) is here e.g. 30 to 200 ml/min.

Figure 4:
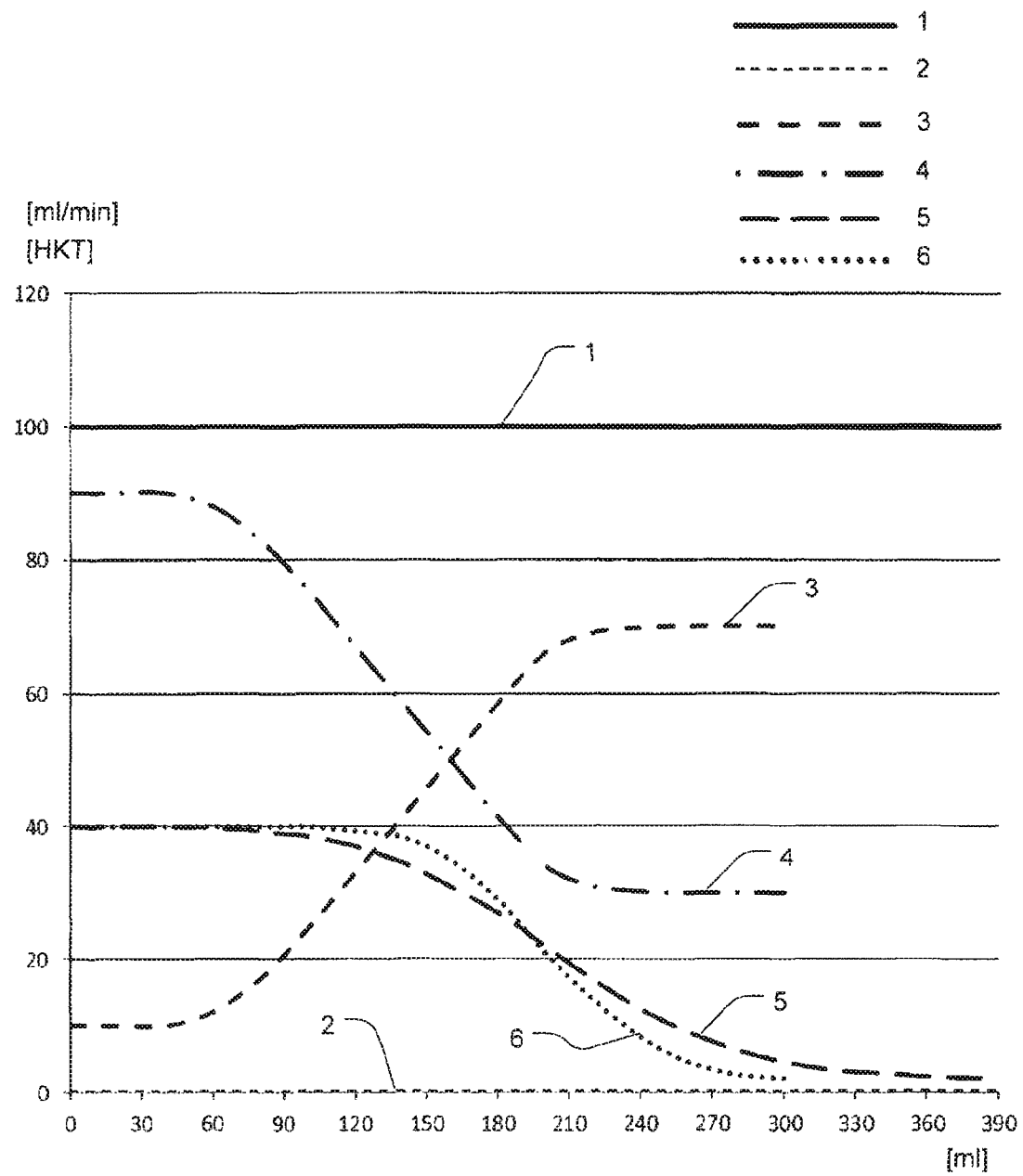
FIG. 4 shows the comparison between a traditional blood return with NaCl and a blood return by means of an example method disclosed herein.

FIG. 4 shows a comparison between a blood return in the prior art and an exemplary embodiment of the method according to the present disclosure.

In this example, the method according to the present disclosure, advantageously reduces the required amount of substituate from the usual 390 ml to only 300 ml.

The continuous line (line 1) describes the flow rate present at the entry of the blood filter 19. This flow rate is optionally unchanged during the entire blood return in both the prior art and in the exemplary method according to the present disclosure and may be 100 ml/min.

In the prior art, the conveying rate of the UF pump during the blood return is 0 ml/min, as seen in the thin, short dashed line (line 2). There is no flow across the filter membrane. Therefore, the flow rate at the entry of the blood filter 19 (line 1) is here the same as the flow rate at the exit of the filter 19.

In the prior art, this results in an absolute hematocrit HKT at the venous patient connection (line 5, long-dashed line), in this case at the venous substituate/blood detector 25, which is 40% at the beginning of the blood return. Due to the desired displacement of the blood by the substituate, the hematocrit HKT decreases at the detector 25 during the blood return until the hematocrit reaches a pre-determined value of e.g. 2% there. In the prior art, 390 ml physiological saline solution must be introduced into the extracorporeal blood circuit in order to reach this value of 2% (see x-axis of the diagram of FIG. 4).

In the embodiment of the method according to the present disclosure which is exemplarily illustrated in FIG. 4, the flow rate at the filter exit (line 4, dot-dashed) is lower than the flow rate at the filter entry (line 1), because the UF pump 40 removes water from the spent dialysate chamber 19b. The flow rate of the UF pump 40 is shown in the bold, short-dashed line (line 3). Here, it is clear that the flow rate of the UF pump 40 increases across or during the blood return (line 3) with the result that the flow rate decreases at the filter exit (line 4). Water is removed from the blood/substituate mixture in the blood filter 19 by the UF pump 40, which causes the hematocrit HKT at the venous patient connection 27 to decrease to the pre-determined value (e.g. 2%) already earlier, namely after infusing only 300 ml substituate (line 6, dashed). Thus, for an almost complete reinfusion of the blood volume contained in the extracorporeal blood circuit 1, less substituate is infused according to the present disclosure than in the prior art.

The present invention is not limited to the above-described embodiments, which are given for illustration only.

LIST OF REFERENCE NUMERALS 1 extracorporeal blood circuit
2 blood cassette
4 treatment apparatus, blood treatment apparatus
5 access device, e.g. arterial connection needle
6 arterial patient hose clamp
7 venous patient hose clamp
8 supply line
9 arterial section or arterial blood line or arterial patient line
11 blood pump
13 addition site for substituate (pre-dilution)
14 addition site for substituate (post-dilution)
15 arterial air/blood detector
17 second conveying device, e.g. a substituate pump
17a substituate line
18 automatic substituate port
19 blood filter, filter
19a blood chamber
19b spent dialysate chamber
21 venous air separator chamber 23 venous section or venous blood line
23a venous section
25 venous substituate/blood detector
26 compressed air source
27 access device, e.g. venous connection needle, venous patient connection
29 control or regulating device
31a fresh dialysate inlet line
31b spent dialysate outlet line
33a, b, c pressure sensors
35 single needle valve
36 single needle chamber
37 pressure sensor
40 ultrafiltration pump (UF pump)
V24 valve
V25 valve
50 bag

The invention claimed is:

1. A method for removing at least one of: blood and a blood mixture from an extracorporeal blood circuit after a blood treatment session of a patient, wherein the extracorporeal blood circuit includes a blood filter comprising:
a blood chamber;
a dialysate chamber; and
a membrane arranged between the blood chamber and dialysate chamber,
wherein the blood filter is fluidly connected to:
an arterial blood line which leads to the blood chamber;
a venous blood line which leads away from the blood chamber;
a dialysate inlet line which leads to the dialysate chamber; and
a dialysate outlet line which leads away from the dialysate chamber,
wherein the method comprises:
displacing the at least one of: the blood and the blood mixture from the blood chamber by introducing substituate contained in a substituate line into the arterial blood line, wherein the introducing substituate comprises operating a substituate pump to convey the substituate contained in the substituate line while the substituate line is connected to a source of substituate; and
generating a pressure difference in the blood filter with a first pressure in the dialysate chamber and a second pressure in the blood chamber, wherein the first pressure is less than the second pressure,
wherein a flow rate ratio of an ultrafiltration pump to a blood pump and a flow rate ratio of the ultrafiltration pump to the substituate pump is in a value range of 0.01 to 0.8, and
wherein the flow rate ratio of the ultrafiltration pump to the blood pump or the flow rate ratio of the ultrafiltration pump to the substituate pump increases during the execution of the method depending on the substituate volume conveyed so far or from beginning the method.

2. The method according to claim 1, wherein no blood is withdrawn from the patient while executing the method.

3. The method according to claim 1, wherein the pressure difference is at least partially generated by at least one pump.

4. The method according to claim 3, wherein the at least one pump is at least one of: the ultrafiltration pump, the substituate pump and the blood pump.

5. The method according to claim 4, wherein the ultrafiltration pump is at least temporarily activated concurrently with the substituate pump and the blood pump.

6. The method according to claim 4, wherein the ultrafiltration pump is at least temporarily activated concurrently with the substituate pump or the blood pump.

7. The method according to claim 1, wherein a flow rate of the blood pump and a flow rate of the substituate pump is between 30 to 280 ml/min.

8. The method according to claim 1, wherein a flowrate of the blood pump or a flow rate of the substituate pump is between 30 to 280 ml/min.

9. The method according to claim 1, wherein the flow rate ratio of the ultrafiltration pump to the blood pump and the flow rate ratio of the ultrafiltration pump to the substituate pump increases during execution of the method depending on the substituate volume conveyed so far or from beginning the method.

10. The method according to claim 1, wherein at least one of the flow rate ratio of the ultrafiltration pump to the blood pump and the flow rate ratio of the ultrafiltration pump to the substituate pump, is varied during the execution of the method in order to control or regulate the hematocrit in the venous bloodline to a predetermined value.

11. The method according claim 1, wherein the flow rate ratio of the ultrafiltration pump to the blood pump and the flow rate ratio of the ultrafiltration pump to the substituate pump is regulated depending on the hematocrit in the venous blood line, which is determined by a venous substituate/blood detector.

12. The method according claim 1, wherein the flow rate ratio of the ultrafiltration pump to the blood pump or the flow rate ratio of the ultrafiltration pump to the substituate pump is regulated depending on the hematocrit in the venous blood line, which is determined a venous substituate/blood detector.

13. A method for removing at least one of: blood and a blood mixture from an extracorporeal blood circuit after a blood treatment session of a patient, wherein the extracorporeal blood circuit includes a blood filter comprising:
a blood chamber;
a dialysate chamber; and
a membrane arranged between the blood chamber and dialysate chamber,
wherein the blood filter is fluidly connected to:
an arterial blood line which leads to the blood chamber;
a venous blood line which leads away from the blood chamber;
a dialysate inlet line which leads to the dialysate chamber; and
a dialysate outlet line which leads away from the dialysate chamber,
wherein the method comprises:
displacing the at least one of: the blood and the blood mixture from the blood chamber by introducing substituate contained in a substituate line into the arterial blood line, wherein the introducing substituate comprises operating a substituate pump to convey the substituate contained in the substituate line while the substituate line is connected to a source of substituate; and
generating a pressure difference in the blood filter with a first pressure in the dialysate chamber and a second pressure in the blood chamber, wherein the first pressure is less than the second pressure,
wherein a flow rate ratio of an ultrafiltration pump to a blood pump and a flow rate ratio of the ultrafiltration pump to the substituate pump is in a value range of 0.01 to 0.8, and wherein at least one of the flow rate ratio of the ultrafiltration pump to the blood pump and the flow rate ratio of the ultrafiltration pump to the substitute pump, is varied during the execution of the method in order to control or regulate the hematocrit in the venous bloodline to a predetermined value.

14. The method according to claim 13, wherein no blood is withdrawn from the patient while executing the method.

15. The method according to claim 13, wherein the pressure difference is at least partially generated by at least one pump.

16. The method according to claim 15, wherein the at least one pump is at least one of: the ultrafiltration pump, the substituate pump and the blood pump.

17. The method according to claim 16, wherein the ultrafiltration pump is at least temporarily activated concurrently with the substituate pump and the blood pump.

18. The method according to claim 16, wherein the ultrafiltration pump is at least temporarily activated concurrently with the substituate pump or the blood pump.

19. The method according to claim 13, wherein the flow rate ratio of the ultrafiltration pump to the blood pump and the flow rate ratio of the ultrafiltration pump to the substituate pump increases during execution of the method depending on the substituate volume conveyed so far or from beginning the method.

* * * * *

UNITED STATES PATENT AND TRADEMARK OFFICE
CERTIFICATE OF CORRECTION

PATENT NO. : 11,116,883 B2
APPLICATION NO. : 16/334092
DATED : September 14, 2021
INVENTOR(S) : Martin Thys Page 1 of 1

It is certified that error appears in the above-identified patent and that said Letters Patent is hereby corrected as shown below:

In the Claims

Column 20, Line 23, Claim 11, after "according" insert --to--.

Column 20, Line 29, Claim 12, after "according" insert --to--.

Signed and Sealed this
Seventh Day of December, 2021

Drew Hirshfeld
*Performing the Functions and Duties of the*
*Under Secretary of Commerce for Intellectual Property and*
*Director of the United States Patent and Trademark Office*